United States Patent [19]

Allington

[11] Patent Number: 4,523,097

[45] Date of Patent: Jun. 11, 1985

[54] METHOD AND APPARATUS FOR REDUCING SCHLIEREN NOISE IN A LIQUID CHROMATOGRAPH

[75] Inventor: Robert W. Allington, Lincoln, Nebr.

[73] Assignee: ISCO, Inc., Lincoln, Nebr.

[21] Appl. No.: 527,954

[22] Filed: Aug. 31, 1983

[51] Int. Cl.³ ............................................ G01N 31/08
[52] U.S. Cl. ................................ 250/458.1; 356/129
[58] Field of Search .......................... 250/458.1, 373; 356/410, 411, 129; 73/61.1 C; 210/656

[56] References Cited

U.S. PATENT DOCUMENTS

| | | | |
|---|---|---|---|
| 4,131,427 | 12/1978 | Karp | 356/129 |
| 4,238,327 | 12/1980 | Liburdy | 210/656 |

FOREIGN PATENT DOCUMENTS

| | | | |
|---|---|---|---|
| 1277812 | 1/1961 | France | 210/656 |
| 474598 | 12/1968 | Japan | 73/61.1 C |
| 474599 | 12/1968 | Japan | 73/61.1 C |

OTHER PUBLICATIONS

Anderson, F. et al., "Automated Detector for Liquid Chromatography", IBM Technical Disclosure Bull., vol. 19, No. 4 (1976).

Primary Examiner—Alfred E. Smith
Assistant Examiner—Richard Hanig
Attorney, Agent, or Firm—Vincent L. Carney

[57] ABSTRACT

A beam of light falling within the range of 180 to 3,000 nanometers is transmitted through a flow cell in an optical compartment of an absorbance detector after warm up of the equipment while the eluant flows through the flow cell from a chromatographic column. The column extends upwardly from the absorbance detector into an air chamber having a volume of approximately 0.25 cubic foot formed with acrylic walls. Air flows from the absorbance detector under the power of a fan at approximately 10 cubic feet per minute upwardly through an air duct having a cross section of approximately 1.5 square inches to the top where it connects with the air chamber, the speed of the motor being adjustable until temperature varies less than one degree Celsius between the flow cell and the lower 10 centimeters of the column. Under these conditions Schlieren noise from the flow cell due to flow-induced thermo-optical effects is reduced.

22 Claims, 3 Drawing Figures

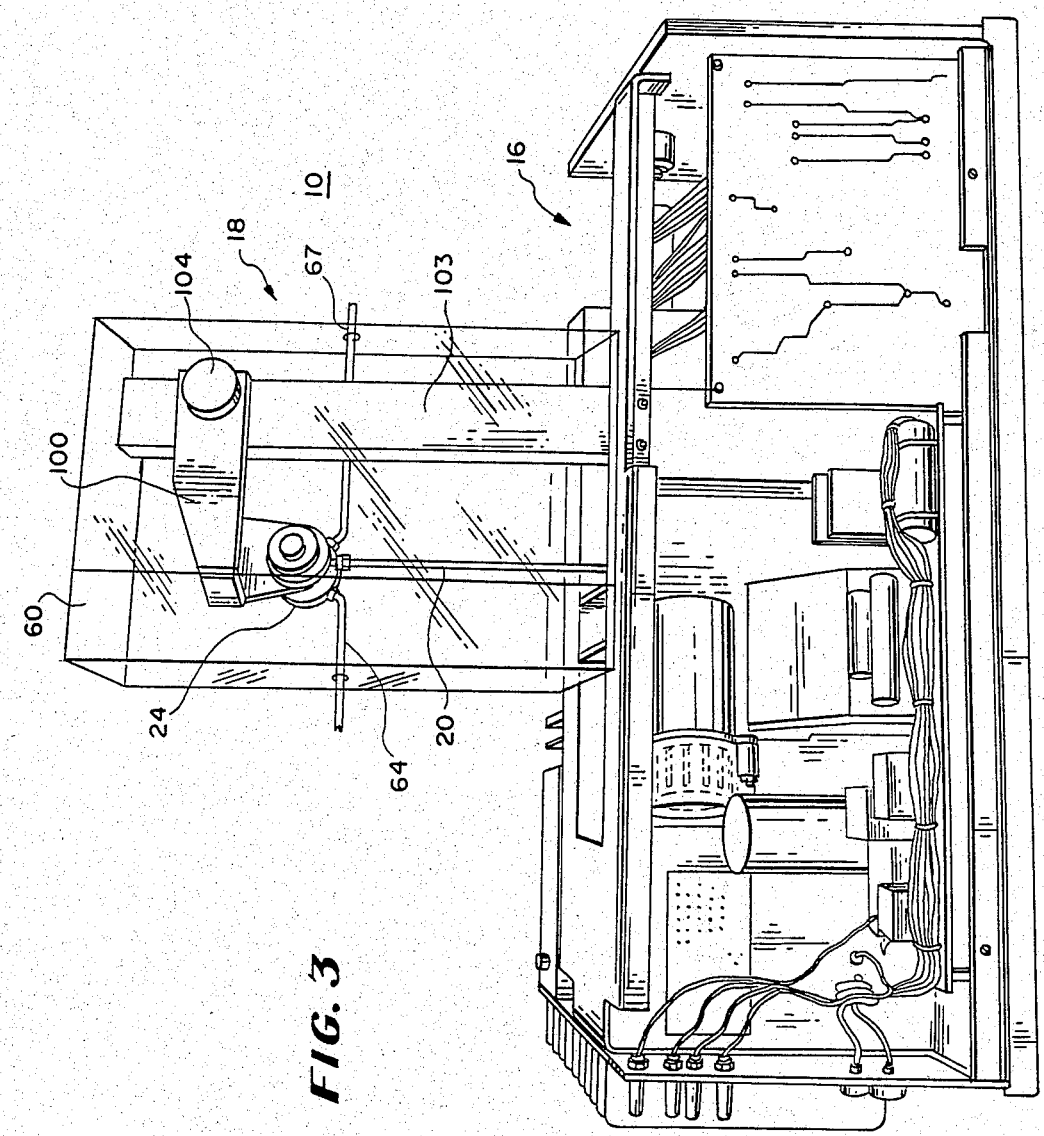

METHOD AND APPARATUS FOR REDUCING SCHLIEREN NOISE IN A LIQUID CHROMATOGRAPH

BACKGROUND OF THE INVENTION

This invention relates to methods and apparatus for reducing Schlieren noise in a liquid chromatograph.

It is known to reduce Schlieren noise in a liquid chromatograph by reducing the temperature differences between the eluate and the flow cell. This reduces the difference in density and hence differences in refraction index between portions of the eluate in the flow cell. Since the eluate is in motion, such differences deflect light in an unpredictable manner, thus producing photometric noise.

The prior art technique attempts to maintain a temperature equality between the flow cell and the eluate entering the flow cell by introducing the eluate into a heat exchanger built into the flow cell. In this technique, the outlet of the heat exchanger is connected to the flow entrance of the flow cell and the body of the heat exchanger is thermally connected to the body of the flow cell. Another technique is to use a conical optical path in the flow cell so that Schlieren scattered light is not absorbed by the cell walls.

The prior art techniques have several disadvantages, such as: (1) a substantial amount of Schlieren noise remains; (2) the absorbance detector causes heat to be conducted to the flow cell and therefore sets up temperature gradients within the flow cell with respect to the flow of eluate; (3) the techniques are slow to stabilize and require much time before measurements can be made without excessive Schlieren noise; and (4) the fluid volume of the heat exchanger or the excess volume of the conical optical path over a cylindrical path degrades the degree of separation of narrow chromatographic peaks or bands in the eluate.

The disadvantage caused by the fluid volume of the heat exchanger or the excess volume of the conical optical path over a cylindrical path is a particular problem with micro-liquid chromatography. A common column diameter for micro-liquid chromatography (MLC) is one millimeter and a common conventional high performance liquid chromatography (HPLC) column diameter is 4.6 millimeters. Thus, the cross sectional area of a MLC column is about one-twentieth (1/20) that of an HPLC column, and so MLC solute peaks are smaller in volume by at least a factor of 20. It is more than a factor of 20 if the length of a peak residing in the column also decreases when going from HPLC to MLC.

Because the solute peaks are smaller in MLC, the peak resolution degradation problems are aggravated because of the difficulty of detecting and collecting low volume bands. This problem is further aggravated when micro-capillary MLC columns with a diameter of 0.1 millimeter or less are used.

The smaller peak volumes of MLC require proportionately smaller fluid volumes in the optical path in order to maintain the same chromatographic resolution. Since shortening the optical path length decreases the absorbance sensitivity according to Beer's Law, the diameter of the path length must be made smaller instead. The greater length to diameter ratio of MLC cells increases their Schlieren noise over that of comparable HPLC cells, thus making it even more of a problem with MLC than with HPLC. The conventional HPLC noise reduction methods are undesirable for MLC because they degrade volumetric resolution which is much more critical for MLC than for HPLC.

SUMMARY OF THE INVENTION

Accordingly, it is an object of the invention to provide a novel liquid chromatograph.

It is a still further object of the invention to provide a sensitive low-noise detector for MLC.

It is a still further object of the invention to provide novel apparatus and methods for removing Schlieren noise while increasing resolution.

It is a still further object of the invention to reduce temperature gradients between the eluate flowing through a flow cell and the temperature of the flow cell.

It is a still further object of the invention to provide a liquid chromatograph with very high resolution.

It is a still further object of the invention to provide a novel apparatus and method for obtaining temperature stability within a heated flow cell and eluate which is received by the chromatograph at ambient temperature.

It is a still further object of the invention to provide a chromatograph with a minimum of degradation of resolution due to the optical cell and the fluid connector between the column and the optical cell.

In accordance with the above and further objects of the invention, a flow cell is mounted within a compartment of an absorbance detector and communicates with a column at least partly within the cabinet of the absorbance detector. The sample injector and any portion of the column extending outside the cabinet are enclosed by an air chamber.

Air is circulated from the absorbance detector to a location near the sample injector and eluant inlet and then forced to flow in the same direction along the column as the eluant toward the flow cell. The circulation of air through the system is at a sufficient rate to stabilize temperature in the system so that it does not vary at any location along the flow path from a point on the column 10 centimeters above the light path of the flow cell to the light path itself by more than 0.2 degree Celsius.

The controlled flow of air from the absorbance detector to the eluant inlet and along the column back to the absorbance detector creates a temperature gradient in the air with the highest temperature being in the cabinet near the fan inlet and where the air leaves the cabinet and the lowest temperature being where the air re-enters and contacts the optical compartment within the cabinet. The eluant enters the column at ambient temperature and heat is transferred to it from the air. Heat is also generated in the column by friction as the mobile phase flows down the chromatographic column and is transferred to the eluant. Heat from the air is also transferred through the walls of the air chamber to the outer environment. The cooled air flows around the optical compartment therein to receive heat therefrom before returning to the interior of the absorbance detector. At the same time the air continues to lose heat to the outer environment through the walls of the cabinet surrounding the optical enclosure.

While the temperature is stabilized, light within a frequency range of 180 to 3,000 nanometers is applied through the light path of the flow cell to detect changes in the absorbance characteristic of the eluate flowing therethrough. Schlieren noise is low under these conditions.

Advantageously, the means for causing air to flow in the chamber moves at least an amount of air through the air chamber each minute equal to the volume of the air chamber. It should also be at least 1/100th of the volume of the absorbance detector cabinet through which the air circulates.

The air chamber extends at least ten centimeters outside of the flow cell enclosure and is sufficiently large to contain at least the parts of the column for a height of 10 centimeters above the flow path and most preferably the entire column and the sample injector that are outside the cabinet. There is a temperature gradient along the flow path of the air in the air chamber of at least one degree Celsius and the warmer air at the eluant inlet and sample injection valve is warmer than the air near the flow cell.

After warm-up, the intensity of the light shining through the flow cell has less than a 10 percent variation per minute and is within the wave length range of 180 nanometers to 3,000 nanometers. It passes through an air space in the optical unit that is substantially undisturbed by the flow of air except for minor air leakage and thermal convection effects. Preferably, the air flows over the outside of the optical compartment to decrease temperature differences in the chamber to reduce the temperature gradients in the path of the light.

From the above description, it can be understood that the apparatus and method for reducing Schlieren noise in a liquid chromatograph has several advantages, such as: (1) it is inexpensive; (2) it aids in providing temperature stability; (3) it is easy to control; (4) it stabilizes within a relatively short period of time; (5) it aids in the reduction in temperature-dependent retention time changes; (6) it greatly reduces Schlieren noise without decreasing chromatographic resolution even for MLC; and (7) it actually increases chromatographic resolution over that of a conventional detector.

SUMMARY OF THE DRAWINGS

The above noted and other features of the invention will be better understood from the following detailed description when considered in connection with the accompanying drawings, which are:

FIG. 3 is a partly broken-away, perspective view of the embodiment of the invention of FIG. 1 from another angle.

DETAILED DESCRIPTION

Figure 1:
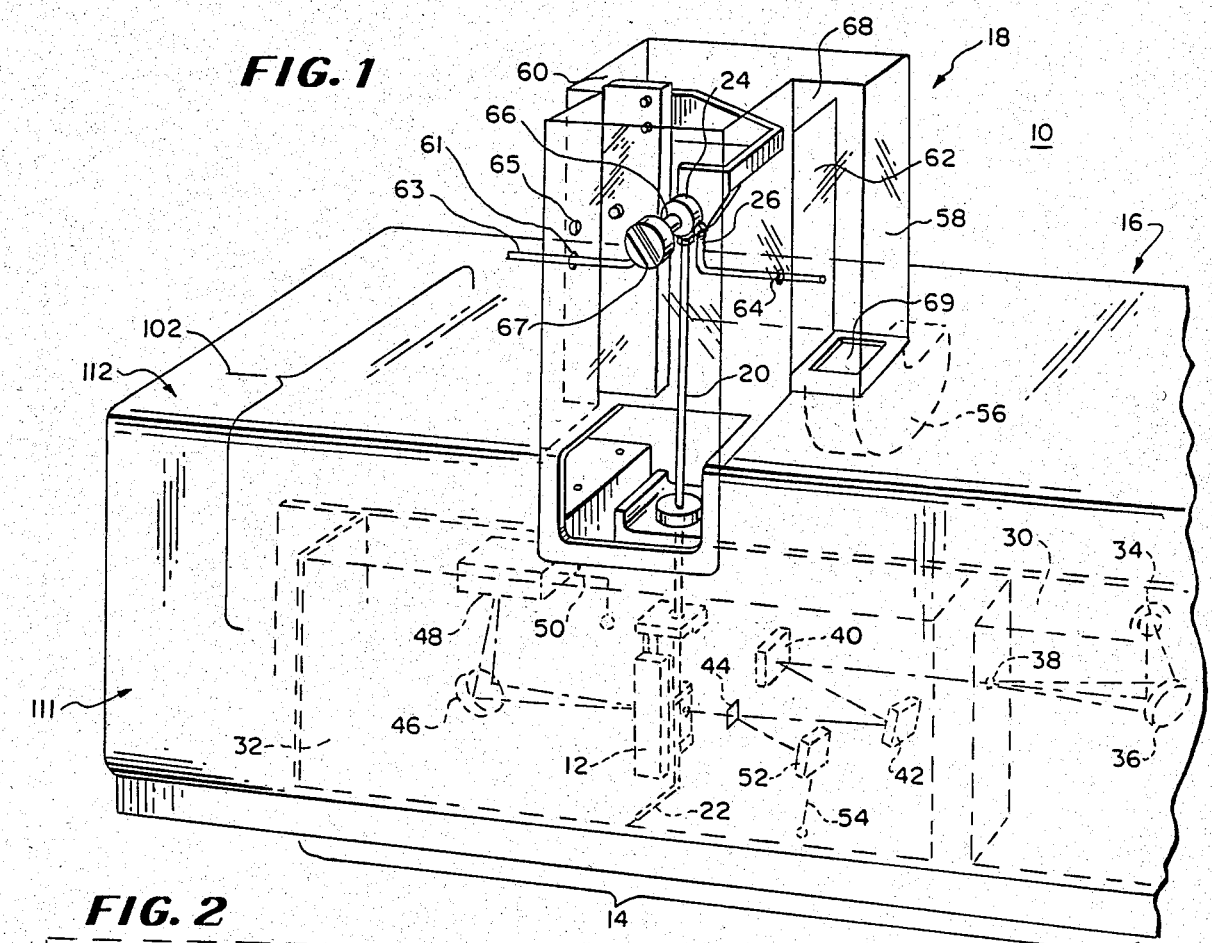
FIG. 1 is a fragmentary simplified perspective view in accordance with an embodiment of the invention.

In FIG. 1, there is shown a simplified perspective view of an apparatus 10 for reducing Schlieren noise in a liquid chromatograph having a flow cell assembly 12, a light path assembly 14, an electro-optical section 16 and an air flow control section 18. The light path assembly 14 generates and transmits light through the flow cell assembly 12 within the electro-optical section 16 while the air flow control section 18 controls the flow of air outside of the electro-optical section 16 to reduce Schlieren noise. Air flow is also controlled by outer wall 111 and upper wall 112 of cabinet 102 surrounding the apparatus below the level of the air chamber 60.

This apparatus 10 has particular application in a micro-liquid chromatograph. Micro-liquid chromatography is a form of high performance liquid chromatography that differs from conventional high performance liquid chromatography in that the inside diameter of the column is substantially less than the usual four to five millimeters.

The flow cell assembly 12 is connected at its top end to a liquid chromatographic column 20 and at its bottom end to an eluate outlet 22. At the upper end of the column 20 is: (1) a sample injection valve 24 for applying samples to the chromatograph for analysis; and (2) a high pressure eluant inlet 26 from a source of eluant which is generally at ambient temperature.

The chromatograph itself may be of any type but the preferred embodiment is directed to a micro-scale, high performance liquid chromatograph such as that described in copending patent aplication Ser. No. 300,567 filed by Robert W. Allington on Sept. 9, 1981 and assigned to the same assignee as this application.

The light path assembly 14 includes a deuterium lamp assembly 30 and an optical compartment 32 mounted side-by-side so that light from the deuterium lamp assembly 30 is transmitted to the optical compartment 32 where it is caused to flow through the flow cell assembly 12 within the optical compartment 32. The deuterium lamp assembly 30 includes a deuterium lamp 34 and an aspheric condensing mirror 36 which focuses light through a small slit at 38 into the optical compartment 32.

The optical compartment 32 is sealed so that air from the air flow control section 18 contacts it on its outer compartment surface but does not flow through the optical path. It includes an aspheric monochrometer focusing mirror 40, a diffraction grating assembly 42 and a beam splitter 44. The aspheric monochrometer focusing mirror 40 is positioned to receive light from the deuterium lamp assembly 30 after it has passed through the slit at 38 and focuses the light upon the diffraction grating assembly 42.

The diffraction grating assembly focuses selected frequencies of light on the beam splitter 44. A portion of the light passing through the beam splitter 44 is transmitted through the flow cell assembly 12 and reflected by the collecting mirror 46 onto a first detector 48 which generates a signal on conductor 50. A second portion of the light from the beam splitter 44 is focused on a second detector 52 resulting in a signal on conductor 54. These signals are used to provide information about the sample as described in the below mentioned patent application and as known in the art.

The electro-optical section 16 includes both the deuterium lamp assembly 30 and the optical compartment 32 as well as the electronic equipment necessary for a typical absorbance monitor resulting in output signals that provide information about the eluate flowing through the eluate outlet 22.

The absorbance monitor in the prefered embodiment is similar to the one disclosed in United States patent application Ser. No. 351,193 filed in the name of Robert W. Allington on Feb. 22, 1982, entitled Absorbance Monitor and assigned to the same assignee as this application. However, the absorbance monitor has been modified to accommodate the chromatographic column and flow cell within the cabinet in the manner shown in FIG. 1 in the preferred embodiment. The specific absorbance monitor is not part of this invention.

The air flow control section 18 includes a blower 56, an air duct 58 and an air chamber 60. The air duct 58 is generally a parallelopiped, being formed of a top and four side walls mounted over an outlet from the cabinet to the electro-optical section 16. The walls are ¼ inch thick and it has a volume of approximately 0.01 cubic foot with the vertical sides being one and one-quarter inches by one and one-eighth inches and the entire air duct 58 being 11½ inches in height. It is positioned against the air chamber 60 and shares a common top with it.

The air chamber 60 encloses the top of the chromatographic column 20, the sample valve 24 and the eluant inlet 26. A connecting wall 62 between the air duct 58 and the air chamber 60 is slightly shorter, forming an open space 68 for communication between the two of approximately one and one-half inches by two inches to permit air to flow from the air duct 58 to the air chamber 60. The volume of the air chamber is approximately 0.25 cubic foot and its walls are approximately ¼ inch thick.

To provide air to the air duct 58 and from there to the air chamber 60, the blower 56 is mounted within the electro-optical section 16 and communicates through the top thereof with the bottom of the air duct 58 through an opening 69. It flows approximately 10 cubic feet per minute through the air duct 58 into the air chamber 60. Air from the air chamber 60 flows downwardly over the top portion of the chromatographic column 20 and back into the electro-optical section 16 where it blows across the surface of the optical compartment 32 to remove heat therefrom.

To enable an operator to use the chromatographic column, the walls of the air duct 58 and air chamber 60 are of acrylic plastic and thus transparent. The walls of the air chamber 60 contain a first opening at 64 through which the eluant inlet 26 passes and a second opening 66 through which the sample valve 24 may be manipulated with knob 67. Sample is loaded into the sample valve by injection from a conventional hypodermic needle introduced through hole 65. Excess sample exits the valve through vent tube 63 which passes through hole 61.

In the preferred embodiment, the ratio of the volume between the air duct 58 and the air chamber 60 is approximately 1 to 25. The ratio of the air duct 58 to the air chamber 60 should be in a range less than a ratio of 1 to 1.5 and more than a ratio of 1 to 300 for efficient operation and the ratio of the air chamber 60 to the volume of the electro-optical section 16 which generates heat should be no greater than 1.5 to 1 and no less than 1 to 30.

The volumetric flow rate caused by the blower 56 should be sufficient to create enough static pressure to force air to circulate and reach equilibrium in a reasonable amount of time. More importantly, it is necessary that the equilibrium temperature distribution and thermal fluxes must meet specific criteria which will be described later, in order to accomplish the objects of the invention. In the preferred embodiment the blower 56 exchanges about 10 cubic feet of air per minute and should have a capacity to change at least one-tenth of the volumetric amount of air in the air chamber 60 and air duct 58 each minute.

In operation, the electro-optical section 16 is operated until temperature equilibrium is reached while the blower 56 is operated. Temperature or heat equilibrium is a condition in which the temperature does not vary more than 0.1 degree Celsius at any location within a one minute period of time. In this condition air flows from the electro-optical section 16 through the air duct 58 into the air chamber 60 through an opening 68 downwardly to the bottom of the air chamber 60 and over the surface of the optical compartment 32 back into the electro-optical section 16 for recirculation.

In the preferred embodiment, it requires three hours from cold start or one hour from a standby warm-up start to reach equilibrium but this is a function of the volume of air, the amount of localized heat released and the rate of amount of air. The air blower may be any suitable commercial unit such as one having a squirrel cage wheel inside a snail housing driven at approximately 2500 RPM by any suitable motor, which may be operated on 25 volts at about 60 milliampers from a low-voltage DC supply.

Air flow through the air control section 18 is approximately 10 CFM (cubic feet per minute), at 0.08 inch static pressure. Generally, the chromatograph is not operated until the temperature has stabilized and at this time there is a change in temperature of the air from the blower 56 to the top of the air duct 58 and as the air drops downwardly from the air chamber 60 to the optical compartment 32 it loses heat to establish an air temperature gradient along the flow path and becomes cooler as it follows that flow path.

The fluid in the flow path traveling along column 20 in the same direction as the heated air driven by fan 56 is pre-heated at the top of the flow path and rises in temperature as it flows along. However, at a distance of about 10 to 20 centimeters above the flow cell, the air has cooled to about the temperature of the fluid in the flow path because the air flow is constantly losing heat to the outside environment through the nearest walls of the air chamber. When the air cools sufficiently, it no longer heats the fluid in the flow path and the temperature of the fluid in the flow path does not change as it flows downwardly from this point.

As the fluid in the column 20 flows down to and inside the light path compartment 14, it starts to pick up heat by thermal conduction from the optical compartment 32 which in turn is being heated by thermal conduction from the electro-optical section 16. At the same time, the air flow continues down around the lower part of the column 20 and around the walls of the optical compartment 32. All this time, the flowing air is still losing heat to the outside environment first through the outer walls of the air chamber 18 and then through outer wall 111 and upper wall 112 of cabinet 102 surrounding the light path assembly 14. The air continues to cool and continues dropping through lower and lower temperatures which are colder than the lower part of the column 20 and the flow cell 12.

The air flow rate and sizes and spacings of the components are such that the thermal equilibrium temperatures of the flowing liquid in the lower part of the column 20 and in the flow cell 12 are equal. This is because at this particular temperature, along all or most of this part of the flow path, the heat lost to the air equals the heat gained by conduction from the electro-optical section 16. The positive and negative heat fluxes are higher near the flow cell 12 than at the lower 10 to 20 centimeters of the column 20 but in both places, the positive and negative heat fluxes external to the flow path are equal for the same temperature inside the flow path.

It is believed that this result can only be obtained using the form of co-current flow heat exchanger described. This is a surprising result as countercurrent flow heat exchangers are universally believed to be more efficient than co-current heat exchangers. In fact, co-current heat exchangers are commonly believed to be the least efficient of all forms of heat exchangers.

When the temperature has stabilized, the chromatograph quickly may be operated so its samples are injected in the sample injection valve 24 while eluant flows through the inlet 26 and downwardly in the column 20 in the same direction as the air flow. As the mobile phase flows downwardly, it is heated to a temperature closer to that within the electro-optical section 16 and thus that of the optical compartment 32 and the flow cell 12.

Heat is transferred into the flow cell 12 by conductance from the electro-optical section 16 but a portion of this heat is absorbed by the air as it flows downwardly around the surface of the optical compartment 32 and back into the electro-optical section 16.

Because additional heat conducted to the optical compartment 32 from the electro-optical section 16 is differentially offset by the increased heat from hotter air flowing through the air duct 58 and the air chamber 60, the equipment is not sensitive to changes once it has stabilized. Thus an increase in heat conducted into the optical compartment 32 is accompanied by an increase in heat convected into the air chamber 60 and the two temperatures stay in balance.

The two temperatures stay in balance because the heat loss of the air through the air chamber walls from the air flowing downwardly through the air chamber maintains itself in the same proportionate increase as the heat lost from the area of the flow cell 12 in the optical unit 32 to the surrounding environment. This balance is maintained because more heat is removed from the area of the flow cell 12 to compensate for an increase in loss through the chamber walls from the air and this maintains stability. Conversely, changes in ambient temperature also have small effect in changing the differential temperature between the flow cell 12 and the column 20 when this differential is initially set to zero by use of the thermal system described herein because reductions in heat loss from the air flowing through the chamber are offset by reductions from the area of the flow cell 12.

Because of the automatic balancing of heat losses, the manual adjustment of the speed of the blower 56 is relatively easily made to obtain stability with a slight difference in temperature between the flow cell 12 and the fluid in the column 20 flowing through the flow cell 12. It is possible to maintain that difference to a value of less than one degree Celsius.

Figure 2:
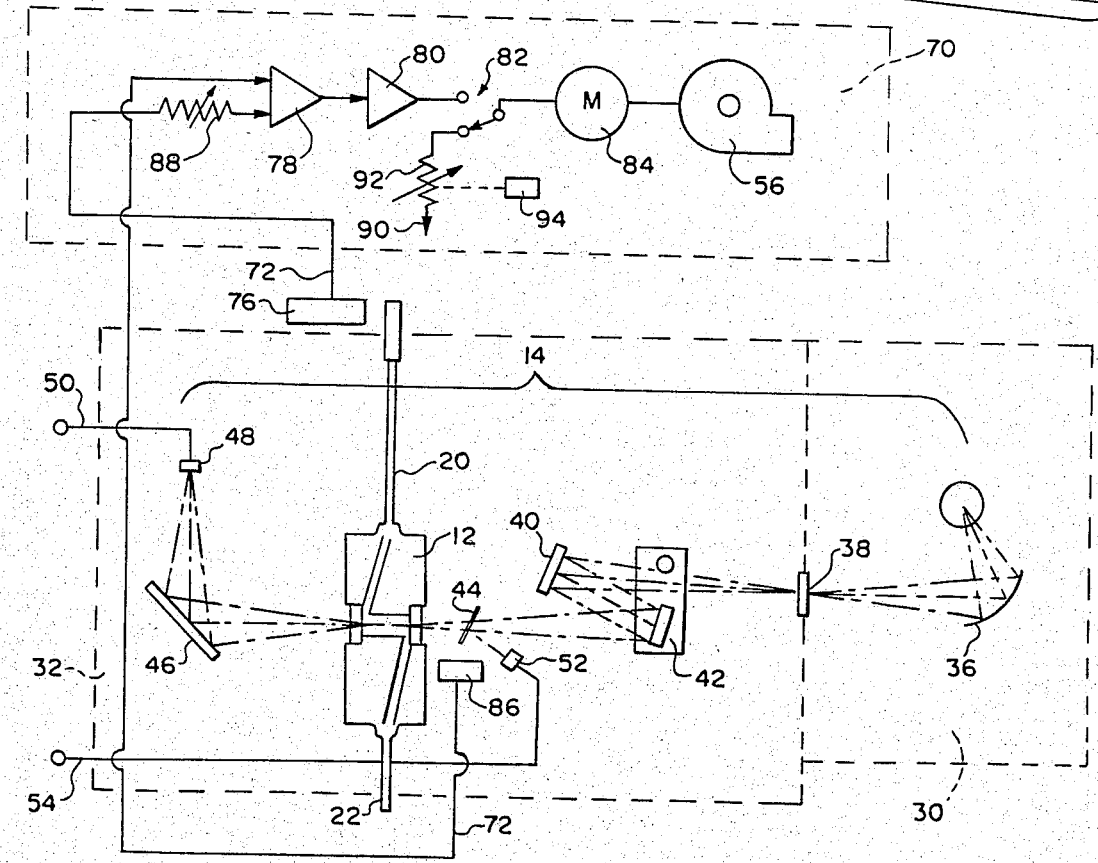
FIG. 2 is a schematic showing of a portion of the embodiment of FIG. 1.

In FIG. 2 there is shown a schematic diagram of the optical compartment 32, the deuterium lamp compartment 30 and a blower control system 70. In one embodiment, the blower control system 70 aids in stabilizing the temperature within the optical compartment to reduce Schlieren noise caused by temperature gradients from heat generated in the deuterium lamp compartment and electro-optical section.

To detect chromatographic peaks, the entrance aperture plate or slot 38 of the optical compartment 32 is positioned between the optical compartment 32 and the deuterium lamp compartment 30 so that light from the deuterium lamp 34 is condensed onto the aperture by the mirror 36 and passes from there into the optical compartment 32 which is next to it. Electrical signals from the optical compartment 32 are conducted outwardly from conductors 50, 54 and 72 with the signal from the conductors 50 and 54 being conducted to the absorbance detector disclosed in the aforementioned patent application and signals from the conductor 72 being conducted to the blower control system 70.

The optical compartment 32 is positioned in the path of air flowing downwardly from the air chamber 60 to be cooled thereby. Within this unit, a small amount of heat may be generated from a tungsten lamp (not shown) which may be used as an alternate source of light to the deuterium lamp 34.

The grating 42 is pivotable to select frequencies of light from either the tungsten lamp or the deuterium lamp 34. This selected frequency of light is transmitted to the beam splitter 44. The beam splitter 44 transmits light in one beam through the flow cell 12 and in another beam to the detector 52. The light flowing through the flow cell 12 is reflected from the collecting mirror 46 onto the detector 48 with the conductors 50 and 54 respectively conducting signals from the detectors 48 and 52.

The apparatus and method of reducing Schlieren noise: (1) produces and stabilizes a temperature gradient of downwardly decreasing temperatures in the air circulating through the system to reduce temperature variations in the column by opposing the downwardly-increasing fluid temperature gradient that would otherwise occur; (2) reduces temperature changes between the various portions of the eluant flowing from the column 20, through the upper part of the flow cell 12, and through the light path of the flow cell, due to an imbalance of net transverse thermal flux at any point along this entire part of the chromatographic flow path to reduce any Schlieren noise; and (3) reduces temperature changes in the air within the optical compartment to reduce extra-flow cell Schlieren noise caused by different density layers of air. The principal effect, however, is noise caused by the fluid flowing through the flow cell 12.

Generally, after the warming up of the light source, the light intensity variations sources in the short term are less low. The variation in light intensity after this warm-up period is less than ten percent within one minute. The absorbance measurements are made more accurately than this so, therefore, it usually requires recourse to a reference photocell or feedback stabilization of the light source in one of the ways known in the art. The frequencies of light which are selected for transmission fall within the range of 180 to 3,000 nanometers.

To adjust the rate of flow of air from the blower 56, the blower control system 70 includes a differential amplifier 78, a power amplifier 80, a switch 82 and the motor 84 for the blower 56. A first temperature measuring device 76 is preferably mounted on the chromatographic column above the flow cell and a second temperature measuring device 86 is mounted within the optical compartment 32, preferably on the flow cell 12 proximate to its light path and connected through conductor 72 to one input of the differential amplifier 78, the other input of which is electrically connected to the temperature measuring device 76, located outside the optical compartment 32 which is the temperature of the eluant in the column 20 (FIG. 1).

With this arrangement, the signals from the temperature measuring devices 76 and 86 are compared in the differential amplifier 78. One input of the differential amplifier 78 is adjustable by a variable resistance 88 connected in circuit with one of the temperature measuring devices 76 and the differential amplifier 78. The temperature measuring device 76 is positioned at a location where it measures column temperature or ambient temperature such as being spaced by insulation or physically spaced from the electro-optical section 16.

To select manual adjustment of the air movement or automatic adjustment, the switch 82 is a single pole, double-throw switch having its switch arm electrically connected to the input of the blower motor 84. One of the contacts against which it may be thrown is connected to the output of the power amplifier 80, the input of which is electrically connected to the output of the differential amplifier 78.

When the switch 82 is connected to the output of the power amplifier, variations from a set point, controlled by the variable resistor 88, cause changes in the speed of the motor 84 and thus increasing stability in temperature. When the walls of the light path of the flow cell are at the same temperature as the eluate entering the flow cell, Schlieren noise is substantially reduced because there are little changes in the density of strata of liquid to cause changes in the refraction of light passing through the flow cell 12.

In the preferred embodiment, because of the ease of obtaining stability with the method and apparatus for reducing Schlieren noise in a liquid chromatograph, the speed of the blower 56 is only controlled manually and changed very infrequently. This may be accomplished in the illustrative embodiment of FIG. 2 by throwing the switch 82 against a second contact connected to a source of potential 90 through a variable resistor 92. The resistance of the variable resistor 92 and thus the blower speed may be adjusted manually from outside of the cabinet through a control knob 94.

With this arrangement, the speed of the blower 56 may be adjusted from the control knob 94 while measuring temperature within the optical compartment 32 or the electro-optical section 16 (FIG. 1) until temperature stability is obtained. By proper sizing of the blower and its motor, the control may be eliminated altogether. Any suitable blower may be used such as, for example, a blower snail equipped with a blower wheel rotated at a fixed speed of 2440 RPM by a motor producing 10 CFM at 0.08 sp. Standard commercial units have provided essentially Schlieren noise-free operation of variable wavelength HPLC detectors equipped with a 5 millimeter length by 0.25 millimeter diameter light path flow cell and the air chamber and other modifications described herein.

In FIG. 3 there is shown a perspective view of the apparatus for reducing Schlieren noise 10 having the air flow control section 18 and the electro-optical section 16 showing the circuitry therein. As best shown in this view, the chromatographic column 20 is mounted to an adjustable arm 100 which may be positioned along a support column 103 which it grips at a fixed location upon tightening of the knob 104.

The arm 100 and support column 103 are enclosed within the air chamber 60 to support the column 20 therein at a fixed height which may be adapted in the preferred embodiment to either 10 centimeter or 25 centimeter columns. With this arrangement, the top of the columns and the sample injection valves may be mounted within the air chamber 60 and controlled by blowing air through the air duct 58 into the air chamber 60 until stability is reached and Schlieren noise reduced. The arm 100 and support column 103 are rigid and rigidly mounted to the frame of the housing. They are made of thermally conductive material to permit easy heat transfer and avoid the establishment of undesirable heat gradients.

From the above description, it can be understood that the apparatus and method for reducing Schlieren noise in a liquid chromatograph has several advantages, such as: (1) it is inexpensive; (2) it aids in providing temperature stability; (3) it is easy to control; (4) it stabilizes within a relatively short period of time; (5) it aids in the reduction in temperature-dependent retention time changes; (6) it greatly reduces Schlieren noise without degrading resolution; and (7) it actually improves chromatographic resolution.

Although in the preferred embodiment the air blows to the top of the air chamber 60 through a vertical air duct 58, it is only necessary for the air to be warmer as it moves along the column and cooler against the flow cell to equalize temperatures. Moreover, the column may be mounted in many different ways and at different elevations with respect to the cabinet.

Although a preferred embodiment of the invention has been described with some particularity, many modifications and variations in the preferred embodiment are possible without deviating from the invention. Therefore, it is to be understood that, within the scope of the appended claims, the invention may be practiced other than as specifically described.

What is claimed is:

1. A method of operating a liquid chromatograph having at least a chromatographic column, a sample injection valve, and a flow cell comprising the steps of:
   applying electrical power to an absorbance detector within an enclosure containing at least the flow cell and a portion of the chromatographic column;
   blowing air from the enclosure into an air chamber that encloses a sample injection valve and at least a part of a chromatographic column and recirculating the air from a location near the sample injection valve along the column toward the flow cell until temperature changes with respect to time at each location are within less than 0.1 degree Celsius within the enclosure and chamber within a one minute time period;
   passing eluant after the temperature has stabilized through the column and flow cell;
   transmitting a beam of light having a wave length within a range of wave lengths of 180 nanometers to 3,000 nanometers through the flow cell from a source of light that varies less than ten percent in intensity in a one minute period; and
   detecting changes in the absorbance of light flowing through said flow cell.

2. A method according to claim 1 in which air is blown from the compartment to the inlet of the chromatographic column and back to the compartment at a rate in the range of 1 to 100 volumes of air per minute for each volume of capacity of the chamber.

3. A method of operating a liquid chromatograph comprising the steps of:
   blowing air along a chromatographic column from an electro-optical compartment and back to the compartment in the same direction the eluant flows in the column; and
   after temperature has stabilized with respect to time in the compartment, performing chromatographic runs.

4. A method according to claim 3 in which:
   the step of blowing air includes the step of blowing air from the compartment into an air chamber having at least a part of a chromatographic column within it and recirculating the air from a point on the column, spaced away from its end closer to the flow cell into juxtaposition with the flow cell until the temperature has stabilized within the air chamber; and transmitting eluant through the column and flow cell after the temperature has stabilized.

5. A method according to claim 4 in which the step of blowing air includes the steps of blowing air from the compartment into an air chamber adjacent to the compartment and recirculating the air along the chromatographic column from a location in the air chamber spaced from the flow cell toward the flow cell until the temperature stabilizes.

6. A method according to claim 5 in which the step of blowing air includes the step of blowing air from the compartment into an air chamber and recirculating the air until the temperature changes with respect to time at each location are within less than 0.1 degree Celsius per minute within the air chamber.

7. A method according to claim 6 including the step of detecting changes in the absorbance of light flowing through said flow cell.

8. A method according to claim 3 in which the step of blowing air includes the step of blowing air from the compartment into an air chamber and recirculating the air until the temperature changes with respect to time at each location are within less than 0.1 degree Celsius per minute within the air chamber.

9. A method according to claim 6 further including the step of detecting changes in the absorbance of light flowing through said flow cell.

10. A method according to claim 3 further including the step of detecting changes in the absorbance of light flowing through said flow cell.

11. A low Schlieren noise liquid chromatograph comprising:
an absorbance detector having an enclosure;
an optical section within the enclosure;
indicating and control circuitry within the enclosure;
a flow cell mounted within said enclosure;
said flow cell being positioned to receive light from said optical section;
means for removing eluant from said flow cell;
a chromatographic column communicating with said flow cell, whereby fluid flows through said chromatographic column and said flow cell;
means for injecting a sample into said column;
an air duct;
means having an inlet and an outlet for forcing air from said compartment into said air duct;
an air chamber;
said air duct and air chamber communicating at their ends away from the control circuitry and optical section;
at least a portion of said chromatographic column extending into said chamber;
internal walls forming a passageway for air to flow from said chamber back into said enclosure and adjacent to said flow cell;
said light generating system including means for generating light with a wave length of between 180 nanometers and 3,000 nanometers and transmitting said light through said flow cell;
said means for generating light including a means for generating light which varies in intensity by less than ten percent in one minute; and
means for applying eluant to the inlet of said column.

12. A low Schlieren noise liquid chromatograph according to claim 11 in which there is a substantially direct connection between said chromatographic column and said flow cell permitting direct communication therebetween.

13. A low Schlieren noise liquid chromatograph according to claim 12 in which substantially all of said column is within said air chamber.

14. A low Schlieren noise liquid chromatograph according to claim 13 in which said means for injecting a sample into said column is within said air chamber.

15. A low Schlieren noise liquid chromatograph according to claim 13 further including a means for recirculating air from said location adjacent to said flow cell back to said air duct.

16. A low Schlieren noise liquid chromatograph according to claim 11 further including:
means for mounting said column; and
said means for mounting said column being formed of a highly heat-conductive, heat-retaining metal.

17. Apparatus for reducing the noise in a liquid chromatograph comprising:
an air enclosure;
an air duct communicating with said air enclosure at a first end;
said air duct and enclosure having a second end adapted to be mounted to an absorbance detector;
means for supporting a chromatographic column at least partly within said air chamber;
means for blowing air from said absorbance detector through said air duct, air chamber and back to said air enclosure; and
means for mounting a flow cell and column so that at least a portion of said column is within said enclosure and a portion of said flow cell and chromatographic column are within said absorbance detector, whereby air flows from said air duct to said chamber and through said chamber against the chromatographic column in the direction fluid flows through said chromatographic column to said flow cell.

18. Apparatus for reducing the noise in a liquid chromatograph according to claim 17 further including an injection valve mounted to said chromatographic column and being within said air chamber.

19. Apparatus according to claim 17 further including:
a flow cell mounted within said enclosure;
light generating apparatus;
said flow cell being positioned to receive light from said light generating apparatus;
a chromatographic column communicating with said flow cell, whereby fluid flows through said chromatographic column and said flow cell;
said light generating system including means for generating light with a wave length of between 180 nanometers and 3,000 nanometers and transmitting said light through said flow cell; and
said means for generating light including a means for generating light which varies in intensity by less than ten percent in one minute.

20. Apparatus according to claim 19 further including means for measuring and adjusting the rate at which said air moves.

21. Apparatus according to claim 20 in which said means for adjusting includes means for measuring the temperature in said air chamber.

22. Apparatus according to claim 20 in which said means for adjusting includes means for increasing said rate automatically when said temperature drops with respect to temperature at a point outside the air chamber and decreasing said rate when said temperature increases with respect to temperature at a point outside the air chamber.

* * * * *